(12) United States Patent
Dahan

(10) Patent No.: US 8,762,177 B2
(45) Date of Patent: Jun. 24, 2014

(54) SYSTEMS AND METHODS FOR IDENTIFYING PATIENT PREFERENCES WITH RESPECT TO MEDICAL TREATMENT ATTRIBUTES

(71) Applicant: LogiPref, Inc., Boston, MA (US)

(72) Inventor: Eliav Dahan, Boston, MA (US)

(73) Assignee: Logipref, Inc., Boston, MA (US)

( * ) Notice: Subject to any disclaimer, the term of this patent is extended or adjusted under 35 U.S.C. 154(b) by 0 days.

(21) Appl. No.: 14/025,209

(22) Filed: Sep. 12, 2013

(65) Prior Publication Data

US 2014/0072939 A1 Mar. 13, 2014

Related U.S. Application Data

(60) Provisional application No. 61/700,806, filed on Sep. 13, 2012.

(51) Int. Cl.
*G06Q 50/00* (2012.01)
*G06Q 50/24* (2012.01)
*G06Q 50/22* (2012.01)

(52) U.S. Cl.
CPC ............... *G06Q 50/24* (2013.01); *G06Q 50/22* (2013.01)
USPC .................................... 705/3; 705/2; 600/300

(58) Field of Classification Search
CPC ............................. G06Q 50/22; G06Q 50/24
USPC .......................................................... 705/2-3
See application file for complete search history.

(56) References Cited

U.S. PATENT DOCUMENTS

| | | |
|---|---|---|
| 8,301,465 B2 | 10/2012 | Janas et al. |
| 8,515,780 B2 | 8/2013 | Soto et al. |
| 2008/0281639 A1 | 11/2008 | Quinn |
| 2010/0114080 A1 | 5/2010 | Theriault |
| 2012/0016690 A1 | 1/2012 | Ramarajan et al. |
| 2012/0047105 A1 | 2/2012 | Saigal et al. |
| 2012/0172674 A1 | 7/2012 | Welz et al. |
| 2012/0316891 A1 | 12/2012 | Friedlander et al. |
| 2013/0102899 A1 | 4/2013 | Vezina |
| 2013/0191159 A1 | 7/2013 | Camacho et al. |

OTHER PUBLICATIONS

Allenby, Greg M., Neeraj Arora, and James L. Ginter (1995), "Incorporating Prior Knowledge into the Analysis of Conjoint Studies," *Journal of Marketing Research*, 32 (May), 152-162.

(Continued)

*Primary Examiner* — Michelle L Le
(74) *Attorney, Agent, or Firm* — Knobbem Martens, Olson & Bear LLP

(57) ABSTRACT

Embodiments facilitate determining patient preferences with respect to treatment attributes. A set of treatment options, comprising attributes, for a medical condition may be accessed. A first subset of treatment options may be selected and displayed to a patient. An indication may be received from the patient of a most preferred treatment option and/or a least preferred treatment option. Using the indications received from the patient regarding the first subset of treatment options, another subset of treatment options may be adaptively selected. An indication from the patient of a most preferred treatment option and/or a least preferred treatment option of the adaptively selected subset of treatment options may be received. Based at least in part on the indications received from the patient, a utility function may be generated. The utility function may be used to generate, optionally in substantially real-time, scoring and/or ranking information with respect to the plurality of attributes.

29 Claims, 12 Drawing Sheets

(56) References Cited

OTHER PUBLICATIONS

Arora, N. and Allenby, G. (1999), "Measuring the Influence of Individual Preference Structures in Group Decision Making," *Journal of Marketing Research*, 36 (4), 476-487.

Bodapati et al., "The Recoverability of Segmentation Structure from Store-Level Aggregate Data," *Journal of Marketing Research*, vol. XLI, pp. 351-364, Aug. 2004.

Carroll, J. Douglas and Paul E. Green (1995), "Psychometric Methods in Marketing Research: Part I, Conjoint Analysis," *Journal of Marketing Research*, 32 (Nov.), 385-391.

Dahan, E. and Hauser, J., "The Virtual Customer," *Journal of Product Innovation Management*, Sep. 2002, pp. 332-353.

Dahan, E. and Mendelson, H., "An Extreme Value Model of Concept Testing," *Management Science*, Jan. 2001, pp. 102-116.

Dahan, E. and Srinivasan, V., "The Predictive Power of Internet-Based Product Concept Testing Using Visual Depiction and Animation," *Journal of Product Innovation Management*, Mar. 2000, pp. 99-109.

Ding, M., Grewal, R. and Liechty, J. (2005), "Incentive-Aligned Conjoint Analysis," *Journal of Marketing Research*, 42 (Feb.), 67-82.

Elrod, Terry, Jordan J. Louviere and Krishnakumar S. Davey (1992), "An Empirical Comparison of Ratings-Based and Choice-Based Conjoint Models," *Journal of Marketing Research*, 29 (Aug.), 368-377.

Gilbride, Timothy and Greg M. Allenby (2004), "A Choice Model with Conjunctive, Disjunctive, and Compensatory Screening Rules," *Marketing Science*, 23(3), 391-406.

Green, Paul E. and V. Srinivasan (1978), "Conjoint Analysis in Consumer Research: Issues and Outlook," *Journal of Consumer Research*, 5, 2, (September), 103-123.

Green, Paul E. and V. Srinivasan (1990), "Conjoint Analysis in Marketing: New Developments With Implications for Research and Practice," *Journal of Marketing*, pp. 3-19.

Griffin, Abbie J. and John R. Hauser (1993), "The Voice of the Customer," *Marketing Science*, Winter, pp. 1-27.

Gross, I. (1972) "An analytical approach to the creative aspects of advertising." *Sloan Management Review* 14(1), pp. 83-109.

Huber, Joel and Klaus Zwerina (1996), "The Importance of Utility Balance in Efficient Choice Designs," *Journal of Marketing Research*, 33, (August), 307-317.

Lenk, Peter J., Wayne S. DeSarbo, Paul E. Green, and Martin R. Young (1996), "Hierarchical Bayes Conjoint Analysis: Recovery of Partworth Heterogeneity from Reduced Experimental Designs," *Marketing Science*, 15, 2, 173-191.

Misra et al., "A New Approach to Estimating Heterogeneity in Marketing Models", Jun. 26, 2012, 34 pages.

Netzer, O. and Srinivasan, V. (2007/2008) "Adaptive Self-Explication of Multi-Attribute Preferences," working paper, Columbia Business School.

Netzer, O., Toubia, O., Bradlow, E., Dahan, E., Evgeniou, T., Feinberg, F., Feit, E., Hui, S., Johnson, J., Liechty, J., Orlin, J., Rao, V. (2009), "Beyond Conjoint Analysis: Advances in Preference Measurement," *Marketing Letters*, 21 pp.

Ofek, Elie and V. Srinivasan (2002), "How Much Does the Market Value an Improvement in a Product Attribute?" *Marketing Science*, 21 (4), 98-111.

Weitzman, Martin L. (1979) "Optimal Search for the Best Alternative," *Econometrica*, 47:3 (May), pp. 641 654.

FIG. 3B

Prostate Cancer Treatment Preference Survey

Introduction | Instructions | Attribute | Choices | Preferences
CHOICES

Please choose the most preferred option below

| Option 1 | Option 2 | Option 3 | Option 4 |
|---|---|---|---|
| Doctors and family support this treatment | Doctors and family support this treatment | Doctors and family do not favor this treatment | Doctors and family support this treatment |
| Sex: Same as before treatment | Sex: Unable to engage in sex | Sex: Same as before treatment | Sex: Unable to engage in sex |
| Treatment requires action within weeks | Treatment requires action within weeks | Treatment allows months or longer for decision | Treatment allows months or longer for decision |
| Urinary: No problems | Urinary: Long-term issues | Urinary: Long-term issues | Urinary: Short-term issues |
| Treatment does NOT require surgery | Treatment does NOT require surgery | Treatment does NOT require surgery | Surgery with some risks and hospital time |
| Bowel: No problems | Bowel: Short-term and frequent bowel movements | Bowel: No problems | Bowel: No problems |
| Lifespan: Live my expected Lifespan | Lifespan: Live my expected Lifespan | Lifespan: Live 5 years fewer than expected | Lifespan: Live 5 years fewer than expected |

Prostate Cancer Treatment Preference Survey

Introduction — Instructions — Attribute — Choices — Preferences

CHOICES

Please choose the most preferred option below

| Option 1 | Option 2 | Option 3 | Option 4 |
|---|---|---|---|
| Doctors and family support this treatment | Doctors and family support this treatment | Doctors and family support this treatment | Doctors and family do not favor this treatment |
| Treatment allows months or longer for decision | Treatment allows months or longer for decision | Treatment requires action within weeks | Treatment requires action within weeks |
| Treatment does NOT require surgery | Treatment does NOT require surgery | Surgery with some risks and hospital time | Treatment does NOT require surgery |
| Sex: Decreased compared to before treatment | Sex: Decreased compared to before treatment | Sex: Decreased compared to before treatment | Sex: Decreased compared to before treatment |
| Urinary: Short-term issues | Urinary: Short-term issues | Urinary: Long-term issues | Urinary: Short-term issues |
| Bowel: Short-term and frequent bowel movements | Bowel: No problems | Bowel: Short-term and frequent bowel movements | Bowel: No problems |
| Lifespan: Live my expected Lifespan | Lifespan: Live my expected Lifespan | Lifespan: Live 5 years fewer than expected | Lifespan: Live 5 years fewer than expected |

FIG. 3G

Prostate Cancer Treatment Preference Survey

Introduction → Instructions → Attribute → Choices → Preferences

INTRODUCTION

Please choose the most preferred option below

| | | | |
|---|---|---|---|
| Doctors and family support this treatment | Doctors and family support this treatment | Doctors and family do not favor this treatment | Doctors and family support this treatment |
| Sex: Unable to engage in sex | Sex: Decreased compared to before treatment | Sex: Decreased compared to before treatment | Sex: Same as before treatment |
| Treatment requires action within weeks | Treatment allows months or longer for decision | Treatment requires action within weeks | Treatment allows months or longer for decision |
| Urinary: Long-term issues | Urinary: Short-term issues | Urinary: Short-term issues | Urinary: Short-term issues |
| Treatment does NOT require surgery | Treatment does NOT require surgery | Treatment does NOT require surgery | Surgery with some risks and hospital time |
| Bowel: No problems | Bowel: No problems | Bowel: Short-term and frequent bowel movements | Bowel: No problems |
| Lifespan: Live my expected Lifespan | Lifespan: Live my expected Lifespan | Lifespan: Live 5 years fewer than expected | Lifespan: Live 5 years fewer than expected |

SYSTEMS AND METHODS FOR IDENTIFYING PATIENT PREFERENCES WITH RESPECT TO MEDICAL TREATMENT ATTRIBUTES

Any and all applications for which a foreign or domestic priority claim is identified in the Application Data Sheet as filed with the present application, are hereby incorporated by reference in their entirety under 37 CFR 1.57.

BACKGROUND

1. Field of the Invention

The present invention is related to determining patients' preferences, and in particular, patient preferences with respect to medical treatment.

2. Description of the Related Art

A given treatment for a medical condition has many attributes. For example, a given medical condition may be treatable by several different interventions, such as medication, surgery, or physical therapy. Different medical interventions may be associated with different side effects. Therefore, it may be challenging to determine which of several treatment options to use in treating a given medical condition for a particular patient.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

Certain embodiments facilitate the determination of a patient's preferences with respect to various attributes of medical treatments.

Certain embodiments facilitate determining patient preferences with respect to treatment attributes. A set of treatment options, comprising attributes (e.g., side effects and other attributes), for a medical condition may be accessed from memory. A first subset of treatment options may be selected and provided for display to a patient. An indication may be received from the patient of a most preferred treatment option and/or a least preferred treatment option from the first subset of treatment options. Based at least in part the indications received from the patient regarding the first subset of treatment options, another subset of treatment options may be adaptively selected. An indication from the patient of a most preferred treatment option and/or a least preferred treatment option of the adaptively selected subset of treatment options may be received. Based at least in part on the indications received from the patient, a utility function may be generated. The utility function may be used to generate, optionally in substantially real-time, scoring and/or ranking information with respect to the plurality of attributes.

Certain embodiments optionally enable an operator/survey designer to trade off accuracy against the number of questions that will be asked a patient in order to determine a patient's preferences.

An example aspect comprises a method of evaluating patient preferences, the method comprising: identifying a set of treatment options for a first medical condition, wherein a given treatment option comprises a plurality of attributes including side effects and attributes other than side effects; identifying a first subset of treatment options from the set of treatment options for the first medical condition; providing for display to a first patient the first subset of treatment options; receiving at a computer system an indication from the first patient of a most preferred treatment option and a least preferred treatment option of the first subset of treatment options, wherein the first patient does not provide additional feedback regarding other treatment options in the first subset of treatment options; identifying a second subset of treatment options from the set of treatment options for the first medical condition, the first subset different than the second subset; providing for display to the first patient the second subset of treatment options; receiving an indication from the first patient of a most preferred treatment option and a least preferred treatment option of the second subset of treatment options, wherein the first patient does not provide additional feedback regarding other treatment options in the second subset of treatment options; based at least in part on the indications received from the first patient regarding the first subset of treatment options and the second subset of treatment options, dynamically generating by the computer system, in substantially real time, a third subset of treatment options from the set of treatment options for the first medical condition, the third subset different than the first and second subsets; receiving an indication from the first patient of a most preferred treatment option and a least preferred treatment option of the third subset of treatment options; based at least in part on the indications received from the first patient regarding the first subset of treatment options, the second subset of treatment options, and the third subset of treatment options, determining, by the computer system, weightings for attributes associated with the set of treatment options; generating in substantially real-time, by the computer system, a utility function based at least in part on the weightings; using, by the computer system, the utility function to generate, in substantially real-time, scoring information, ranking information, or both scoring information and ranking information with respect to the plurality of attributes of the set of treatment options; optionally reporting, in substantially real-time, by the computer system, at least a portion of the scoring information, ranking information, or both scoring information and ranking information.

An example aspect comprises a system, comprising: a computing device comprising one or more processors; a non-transitory data store coupled to the processing device, the data store storing a set of treatment options for a first medical condition, wherein a given treatment option comprises a plurality of attributes including side effects and attributes other than side effects; a display interface coupled to the computing device; non-transitory media that stores program code that when executed by the computing device causes the system to perform operations comprising: accessing, from the non-transitory data store, a first subset of treatment options from the set of treatment options for the first medical condition; causing, using the display interface, the first subset of treatment options to be displayed to a first patient; instructing the first patient to select a most preferred treatment option, a least preferred treatment option, or a most preferred treatment option and a least preferred treatment option of the first subset of treatment options; receiving an indication from the first patient of a most preferred treatment option, or a least preferred treatment option, or a most preferred treatment option and a least preferred treatment option of the first subset of treatment options, wherein the first patient does not provide additional feedback regarding other treatment options in the first subset of treatment options; identifying a second subset of treatment options from the set of treatment options for the first medical condition, the first subset different than the second subset; causing, using the display interface, the second subset of treatment options to be displayed to the first patient; receiving an indication from the first patient of a most preferred treatment option, or a least preferred treatment option, or a most preferred treatment option and a least preferred treatment option of the second subset of treatment options; based at least in part on the indications received from the first patient regarding the first subset of treatment options and the second subset of treatment options, dynamically generating, in substantially real time, a third subset of treatment options from the set of treatment options for the first medical condition, the third subset different than the first and second subsets; receiving an indication from the first patient of a most preferred treatment option, or a least preferred treatment option, or a most preferred treatment option and a least preferred treatment option of the third subset of treatment options; based at least in part on the indications received from the first patient regarding the first subset of treatment options, the second subset of treatment options, and the third subset of treatment options, generating in substantially real-time a utility function; using the utility function to generate, in substantially real-time, scoring information, ranking information, or both scoring information and ranking information with respect to the plurality of attributes of the set of treatment options; reporting, in substantially real-time, by the computer system, at least a portion of the scoring information, ranking information, or both scoring information and ranking information.

An example aspect comprises a non-transitory media that stores program code that when executed by a computing system causes the computing system to perform operations comprising: accessing, from a non-transitory data store storing a set of treatment options for a first medical condition, wherein a given treatment option comprises a plurality of attributes including side effects and attributes other than side effects, a first subset of treatment options from the set of treatment options for the first medical condition; enabling the first subset of treatment options to be displayed to a first patient; instructing the first patient to select a most preferred treatment option, a least preferred treatment option, or a most preferred treatment option and a least preferred treatment option of the first subset of treatment options; receiving an indication from the first patient of a most preferred treatment option, a least preferred treatment option, or a most preferred treatment option and a least preferred treatment option of the first subset of treatment options; identifying a second subset of treatment options from the set of treatment options for the first medical condition, the first subset different than the second subset; enabling the second subset of treatment options to be displayed to the first patient; receiving an indication from the first patient of a most preferred treatment option, a least preferred treatment option, or a most preferred treatment option and a least preferred treatment option of the second subset of treatment options; based at least in part on the indications received from the first patient regarding the first subset of treatment options and the second subset of treatment options, dynamically generating, in substantially real time, a third subset of treatment options from the set of treatment options for the first medical condition, the third subset different than the first and second subsets; receiving an indication from the first patient of a most preferred treatment option, a least preferred treatment option, or a most preferred treatment option and a least preferred treatment option of the third subset of treatment options; based at least in part on the indications received from the first patient regarding the first subset of treatment options, the second subset of treatment options, and the third subset of treatment options, generating in substantially real-time a utility function; using the utility function to generate, in substantially real-time, scoring information, ranking information, or both scoring information and ranking information with respect to the plurality of attributes of the set of treatment options; reporting, in substantially real-time, by the computer system, at least a portion of the scoring information, ranking information, or both scoring information and ranking information.

BRIEF DESCRIPTION OF THE DRAWINGS

Embodiments will now be described with reference to the drawings summarized below. These drawings and the associated description are provided to illustrate example embodiments, and not to limit the scope of the invention.

FIGS. 3A-I illustrate example user interfaces.

DETAILED DESCRIPTION PREFERRED EMBODIMENTS

Figure 1:
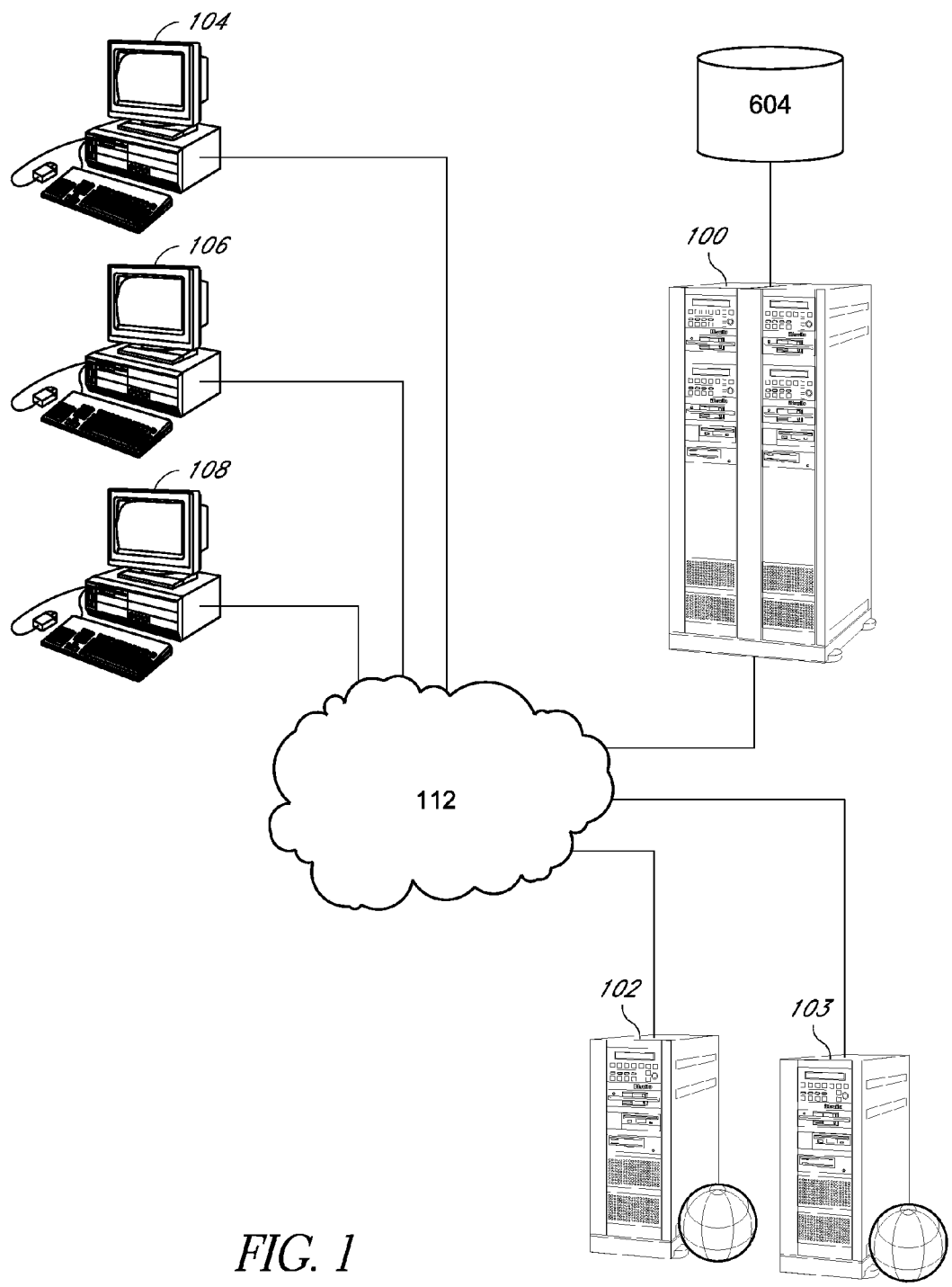
FIG. 1 illustrates an example architecture.

A given treatment for a medical condition has many attributes. For example, a given medical condition may be treatable by several different interventions, such, by way of example, medication, surgery, radiation, devices, or physical therapy. Different techniques may be associated with different side-effects.

For example, a first treatment for prostate cancer may employ surgery, and may result in decreased sexual activity and a reduction in life span of 5 years. A second treatment for prostate cancer may employ radiation, but no surgery, and may eliminate the patient's ability to engage in sexual activity, and result in a reduction in life span of 2 years. For some patients, having increased lifespan may be more important than being able to engage in sexual activity, while for other patients, the ability to engage in sexual activity may be more important than increased lifespan. Some patients will want to avoid surgery, no matter the consequences. Therefore, determining the most suitable treatment for a given patient often does not involve simply determining which treatment is most likely to successfully treat the medical condition, but instead involves evaluating a multiplicity of tradeoffs. In addition, doctors may need to take the patient's goals, fears, dislikes, and other preferences into account when selecting the medical treatment.

However, some patients have difficulty in communicating their preferences to a doctor. For example, some patients may be embarrassed to discuss certain fears, or to discuss concerns regarding sexual activity. Further, patients may be overwhelmed by the number of factors they need to take into account in order to select a given medical treatment from a multiplicity of available treatments. Further, doctors' caseloads are becoming ever heavier, and so doctors have less time to spend with patients to understand patients' fears, goals, and dislikes.

Certain embodiments, utilizing a patient preference evaluation system, address the foregoing challenges, and facilitate the quick and efficient determination of a patient's preferences (e.g., desires and/or dislikes) with respect to medical treatment attributes (e.g., side effects and other treatment issues), without overwhelming the patient with complex demands for information. Certain embodiments efficiently obtain patient feedback with respect to treatment options (e.g., alternative bundles of attributes), optionally generate a utility function which includes treatment attribute weightings (e.g., reflecting the positive or negative importance to the patient) personalized to the patient, and generate scores and/or other summary reflecting the patient's preferences with respect to the treatment attributes.

Example techniques for obtaining patient feedback with respect to treatment options will now be described. Certain techniques do not require that a patient provide an individual score or ranking with respect to each treatment option or treatment option attribute, yet can calculate, optionally for each treatment option attribute, a score/ranking indicating the suitability of the treatment option attribute with respect to the patient' preferences (e.g., the patient's desires, fears, and/or dislikes). For example, the scoring may indicate that an attribute relating to lifespan is more important than an attribute related to sexual activity, or that an attribute related to surgery is more important than an attribute related to incontinence. Thus, a doctor may use such preference information to identify suitable medical treatments that have attributes that match, or that reasonably match the patient's preferences.

Certain embodiments present a patient with multiple options (e.g., in the form of alternative bundles of treatment attributes) at the same time with respect to treatments for a medical condition, wherein the user is asked to provide feedback regarding one or more of the presented treatment options (but optionally not all of the treatment options).

For example, if there are x number of treatment options (sometime referred to herein as the "pool of treatment options", wherein a given treatment option may comprise a bundle of treatment attributes) comprising respective attributes (e.g., side effects, treatment issues, etc.), a first subset of the x number of treatment options may be selected to be presented to the user at the same time. In certain optional embodiments, the options selected to be included in the first subset may include an anticipated (e.g., based a survey of past patients and/or intuition) highly desirable treatment option and an anticipated highly disfavored treatment option, as well as treatment options that are anticipated to be more "in the middle" (neither highly desirable or highly disfavored). It is understood that such anticipations may be generalized to a large set of patients and not to the individual patient, and hence such anticipations may or may not be reflective of the individual patient's personal preferences.

Each option in the first subset of treatment options may be displayed with various attributes associated with the option, such as recovery time, urgency in beginning the treatment, need for surgery, need for medication, effect on lifespan, opinions of doctors, opinion of patient's family, and/or other attributes. For example, certain embodiments may present four medical treatment options (each option comprising a bundle of treatment attributes), from a larger number of treatment options, at a time. Presenting the patient with four choices of treatment options ensures that there are not so many choices that the patient would be overwhelmed, yet not so few that the process of determining the patient's preferences will take too many iterations, too much time, will bore the patient, and will cause the patient to fail to complete the preference survey. However, optionally fewer or more treatment options may be presented at a time (e.g., 2, 3, 5, 6, or 8).

The presented treatment options may or may not specifically detail the associated medical treatment, but will detail one or more treatment attributes. For example, a given treatment option may or may not specify the type of medication that will be used, but may specify the side effects of such medication (e.g., dizziness, reduced sex drive, upset stomach, etc.). The attributes may comprise, at least in part, treatment issues that may optionally be determined, at least in part, from interviews with previous patients, such as in a "voice of the patient" survey, where patients are asked to identify treatment issues that they are concerned with (e.g., does treatment involve surgery, following doctor's advice, sense of urgency to begin treatment, etc.). Other attributes may be determined from recorded side effects that previous patient's experienced with respect to a given treatment.

Optionally, rather than asking the patient to rank or score each of the first subset of treatment options with respect to each other, or ranking a given attribute, the patient may be instructed to identify the best/most preferred choice among the options displayed and/or the worst/least preferred choice. Thus, the patient may optionally be asked to provide feedback specific to two of the presented first subset of treatment options without being asked to provide specific feedback on the other options presented with the best and worst options, and optionally without being asked to provide feedback on an individual attribute (as opposed to the bundle of attributes). The patient's feedback is received by the system and will be processed as discussed below and elsewhere herein.

In addition to the first subset of treatment options, other subsets of treatment options may also be selected from the pool of treatment options. Such selections may be performed prior to the first subset of options being presented to the patient or after the first subset of options is presented to the patient. A given subset of treatment options may optionally be dynamically and adaptively selected from the pool of treatment options based, in whole or in part, on patient feedback for one or more previous subsets of treatment options presented to the patient.

Example processes and techniques will now be discussed in greater detail.

An example embodiment optionally utilizes an Adaptive Best-worst Conjoint (ABC) technique and/or a Conjoint Adaptive Ranking Database System (CARDS) technique to adaptively select what choices (subsets of treatment options) are to be presented to a patient. Using such techniques, a patient preference evaluation process may surprisingly be able to generate accurate rankings/scores for a patient for a multiplicity of treatment options, each comprising multiple attributes, while asking the patient to provide relatively little feedback. With this approach, in certain optional applications, utility functions with 7-10 parameters are estimated in substantially real-time at the patient level with as few as 12-15 tasks (where each task has the user indicate a most preferred option and a least preferred option with respect to a set of about 4 treatment options, where each treatment option comprises 7-10 attributes) which the patient may complete in 10 minutes or less.

For example, a treatment option utility function may optionally be in the form of:

$$\begin{aligned}\text{Treatment option utility} = &\ \text{attributelevel1*weighting1} + \\ &\ \text{attributelevel2*weighting2} + \\ &\ \text{attributelevel3*weighting3} + \\ &\ \text{attributelevel4*weighting4} - \\ &\ \text{attributelevel5*weighting5} - \\ &\ \text{attributelevel6*weighting6} - \\ &\ \text{attributelevel7*weighting7}\end{aligned}$$

Where an attribute level may correspond to a degree or variation of the attribute. For example, if the attribute is "sexual function" side effect, the attribute level may be "1" (corresponding to no sexual function as a result of the treatment), "2" (corresponding to a moderate decrease in sexual function as a result of the treatment), or "3" (corresponding to no impact on sexual function as a result of the treatment).

Utility may be estimated using one or more techniques, such as a best fit linear technique (e.g., OLS (Ordinary Least Squares)), a choice based technique (e.g., LOGIT/Maximum Likelihood), population statistics (e.g., Hierarchical Bayes), optimization (e.g., LINMAP (Linear Programming Technique for Multidimensional Analysis of Preference)), etc. For example, using OLS, the unknown parameters may be estimated in a multiple linear regression model. The sum of squared vertical distances between the observed responses in the dataset and the responses predicted by the linear approximation may be minimized. The resulting estimator can be expressed by a formula, which in certain cases may be a relatively simple formula.

Such a utility function may generate a score for a given bundle of treatment attributes, and the scores may be used to rank the treatment attributes (and optionally the treatments themselves). Such rankings and/or scores may be presented to the patient and/or doctor in a report and may be used as an aid in selecting a treatment. Optionally, the most highly rated treatment option(s) may be identified by the system as a recommended treatment option. Further, by reading the report and discussing the report with the patient, the doctor will better understand the patient's concerns, fears, and desires, and the patient will feel that the doctor understands the patient's concerns, fears, and desires with respect to the medical treatment, improving patient satisfaction with the treatment and with the doctor, surprisingly even if the doctor recommends a treatment that has attributes the patient disfavors.

An example Adaptive Best-worst Conjoint (ABC) process will now be described. In the following description, the phrase "cards" or stimuli is used. By way of example, a card may correspond to a bundle of treatment attributes (e.g., side-effects and/or other issues) for treatment for a medical condition, optionally with or without specifics regarding the treatment itself (e.g., without specifying a specific type of surgery and/or medication, although optionally such specifics may be included in the card). For example, with respect to prostate cancer, a treatment card may include treatment side-effects (e.g., regarding sex, urinary issues, bowel issues, lifespan issues, etc.), whether the doctor or family support the treatment, treatment initiation timing (e.g., whether the treatment requires that the patient begin the treatment process in the very near term or whether the patient can begin the process in several months), whether the treatment involves surgery and hospitalization, etc. It is understood that a "card" does not have to be a physical card and does not have to appear as a card. A card may be in electronic form, displayed on a terminal display, and may be in a form indicating which attributes are associated with which a given treatment option (e.g., where a first card may indicate that a first treatment involves surgery, and a second card may indicate that a second treatment does not involve surgery). A given bundle of treatment attributes may or may not be associated with an actual treatment. As discussed elsewhere herein, the bundles of attributes may be assembled to reduce the amount of feedback needed from the patient needed to score/rank the attributes, rather than be associated with a single actual treatment.

The patient will be presented with multiple treatment cards from which the patient is to choose the most preferred (the "best") card and/or the least preferred card (the "worst"). In the following example, only 16 cards (corresponding to 16 treatment options/attribute bundles) are used. However, other examples may use fewer or additional cards. Certain embodiments optionally limit the number of cards/stimuli (treatment options) to between 16 and 32 to reduce the number of questions the patient needs to answer while still providing a sufficiently accurate evaluation of the patient's preferences with respect to treatment options, although fewer or greater numbers of cards may be used. Certain embodiments, utilizing adaptive algorithms, facilitate the use of many more treatment cards because the adaptive algorithms do not require a patient to view every card in order to provide a sufficiently accurate evaluation of the patient's preferences with respect to treatment options.

The 16 cards in this example may optionally be utilized to provide a rank ordering and/or scores indicating an order of treatment preferences for the patient.

State 1: Given n cards, there are n(n-1)/2 pairs of cards. The process generates a list of possible pair combinations (e.g., all possible pair combinations). The process generates, and optionally makes a list of such pairs. For example, with 16 cards, applying the foregoing formula, the process generates 120 pairs (1-2, 1-3, . . . , 15-16). There may be a patient card preference within each possible pair of cards, or the patient may have no preference for a given pair of cards.

State 2: Optionally, a certain number of choice questions (e.g., subsets of treatment options where the patient is to identify the best and/or worst option) may be presented to the patient in a fixed, predetermined manner (where the choices presented in the question are not adaptively based on choices the patient made in response to previous choice questions), and a certain number of choice questions may include adaptively generated choices (where the choices presented in the question are adaptively based at least in part on choices the patient made in response to one or more previous choice questions).

Optionally, Dawes Rule may be used to design the initial choice questions C/n sets of choice questions (where C=the number of possible cards, and n=the number of alternatives per choice question), as similarly discussed elsewhere herein. A point may be assigned to each positive attribute level for each card, where an attribute level may be considered positive if substantially all or a large majority of patients (e.g., at least 75% or at least 85%) would prefer the attribute level (e.g., where if the attribute is urinary function, and the attribute levels may include "no impact on urinary function" and "treatment will result in the patient needing to wear a diaper," the attribute level "no impact on urinary function" will be assigned a point, and the attribute level "treatment will result in the patient needing to wear a diaper," will not be assigned a point). Whether an attribute level is determined to be positive or not may be determined intuitively and/or based on a survey of patients or potential patients. The points for each card may be totaled, and then the cards may be ranked by total score. Based at least in part on the card scores, one of the four highest scored cards, one of the four lowest scored cards, and two of the middle eight scored cards may be selected for inclusion in a given choice question (assuming the choice question includes 4 choices).

For example, if it is desired to have four alternative options (bundles of attributes) per choice question, optionally the first n/4 questions, in this example 16/4=4 questions, may be fixed, optionally with each of the n cards presented in at least one choice question. Thus, different patients with the same medical issue may optionally be shown the same initial choice questions (4 in this example), and thereafter the choice question sets may be dynamically customized for each patient based at least in part on the patient's responses to the initial choice questions (and optionally on subsequent choice questions). Optionally, all of the cards will be included in at least one of the initial "fixed" choice questions.

In this example, each of the four choice questions in the first series of questions may present a set 4 cards to the patient, and the patient may be asked to select a best/most preferred card (a best bundle of treatment attributes) and a worst/least preferred card (a worst bundle of treatment attributes) for each choice question. In this example, the patient's answers to the first four questions will identify 4 bests, 4 worsts, and 8 middles (which were not chosen as the best or worst treatment option).

For example, the patient may be presented with the treatment cards as follows:
Question 1: Cards 1, 5, 9, 13
Question 2: Cards 2, 6, 10, 14
Question 3: Cards 3, 7, 11, 15
Question 4: Cards 4, 8, 12, 16

If, in response to question 1, the patient selects Card 1 as the best and Card 5 as the worst, and in response to question 2, the patient selects Card 2 as the best and Card 14 as the worst, and in response to question 3, the patient selects Card 7 as the best and Card 11 as the worst, and in response to question 4, the patient selects Card 16 as the best and Card 4 as the worst, then Cards 1, 2, 7, 16 are identified as "bests", Cards 5, 14, 11, 4 are identified as "worsts", and Cards 3, 6, 8, 9, 10, 12, 13, 15 are identified as "middles".

Optionally, fewer or additional questions/subsets may be fixed (not adaptively selected based on the patient's previous best/worst feedback).

State 3: The process then optionally adaptively selects choices for the second series of questions based at least in part on the choices the patient made in response to the first series of questions. For example, the next series of questions may include n/4 questions, although fewer or additional questions may be used. In this example, the four "best" selections made by the patient at state 2 may be included in one choice question, the four "worst" selections may be included in another choice question, and a "middle" from each of the choice questions from state 2 may be grouped together in two more choice questions.

For example, the choice questions may be as follows:
Question 5: Cards 1, 2, 7, 16
Question 6: Cards 3, 6, 8, 9
Question 7: Cards 10, 12, 13, 15
Question 8: Cards 4, 5, 11, 14

State 4: The second series of choice questions are presented to the patient.

The patient may again be asked to select the best and worst with respect to the choices presented by each selection.

State 5: Each of the initial 8 questions asked at states 2-4 resolved 5 distinct pairs. For example, with respect to question 1, from the patient's answer it is determined by the system that the patient prefers card 1 (treatment 1) over card 9 (treatment 9), card 1 over card 13, card 1 over card 5, card 9 over card 5, and card 13 over card 5. Thus, in this example, with the patient providing 16 preference indications (8 best and 8 worst indications) we have determined the patient's preferences with respect to 40 pairs (8 questions×5 pairs resolved/question) out of the 120 possible pairs. An indication as to which pairs of cards are resolved and, in a given pair, which card (treatment) the patient prefers, is stored in a data store, such as a database.

Optionally, additional pairs may be resolved by applying transitivity. A relation is transitive if when A is related to B and B is related to C, then A is related to C. For example, if, via the foregoing questions, it is determined that the patient prefers card 12 over card 15, and card 15 over card 11, then the process can infer that the patient will or is likely to prefer card 12 over card 11. An indication as to which pairs of cards are resolved via transitivity, and, in a given pair, which card the patient prefers, is stored in the data store.

Even with transitivity applied, many pairs may still remain unanswered at this point (e.g., the system has not yet been able to determine whether the patient prefers treatment option A over B or B over A yet). Optionally, the process analyzes the pairs not yet resolved and adaptively assembles additional sets of 4 of the 16 cards to resolve unresolved pairs in an efficient, and optionally the most efficient way so as to resolve the greatest number of unresolved pairs (where the patient has not yet provided an indication as to which of the pair the patient prefers). Based on the analysis, the process generates the next question and stores the patient's choices.

State 5. The process of state 4 may be repeated, where the next choice question is based at least in part on previous choice(s) of the patient. The process may continue repeating state 4 until all or a desired number/percentage of the card pairs are resolved. Optionally, if there is a "tie" between 2 cards, which the patient appears to prefer neither over the other, one card may be arbitrarily designated as preferred with respect to the other card.

Adaptive Best-worst Conjoint, with four options presented at a time, identifies five of the six possible paired comparisons (Best>option B, Best>option C, Best>Worst, option B>Worst, option C>Worst; only B is not compared to C). Thus, ABC in this example is 66% more efficient than traditional choice-based conjoint even without adaptive questioning. This efficiency advantage of best-worst questioning is optionally further enhanced through adaptive questioning based on transitivity of preference. That is, we assume that if full-profile A is preferred to full-profile B, and if B>E, then A is also >E, even though we never directly compared A to E. Such transitivity may resolve even more paired comparisons than direct questioning. For example, with 16 cards, there are 16×15/2=120 possible paired comparisons, over 50% of which are resolved through transitivity.

Optionally, in addition to or instead of the one or more of the techniques described above, card pairs may be resolved via a consistency analysis, described below.

As noted above, CARDS may optionally be used instead of or in addition to ABC. CARDS may be used to specify a finite number of patient types, reducing the number of potential utility functions and making it more efficient to determine patient preferences with respect to treatment attributes. This is in contrast to many conventional techniques, which assume that there are virtually an infinite number of patient types. Thus, certain embodiments enable a much quicker and less computer resource intensive technique as compared to conventional approaches, which may require that a system estimate virtually an infinite number of possible utility functions. A CARDS database may include multiple records, one per scoring rule/utility function, wherein each row includes a rank ordering of the stimuli/cards according to that record's rule. In the example embodiment, the CARDS database of possible rules can derive a discretized version of the continuous multi-dimension space of possible utility functions (e.g., where there may be one dimension per attribute, such as having 7 dimensions for 7 attributes). The database may take each discrete portion of graphed space (e.g. a cube) and summarize that discrete portion with a single, representative utility function. Optionally, different sizes may be used for different discrete portions (e.g., different cube sizes). For example, smaller discrete portions (e.g., cubes) may be used where greater refinement is desired for certain combinations of attributes, such as where it may be predicted (e.g., based on intuition/common sense or previous survey) that such attribute combinations will be more likely to be desirable to patients. Similarly, larger discrete portions may be used where less refinement is desired or needed for certain combinations of attributes, such as where it may be predicted (e.g., based on intuition/common sense or previous survey) that such attribute combinations will be less likely to be important to patients Optionally, the system does not know details regarding real or specific patients, but divides patients into a certain number of types without such knowledge. A given patient type may be associated with a specific ranking of attributes with respect to how important those attributes are to the patient type. For example, a first patient type may be defined as having lifespan as the most important attribute, ability to engage in sex as the second most important attribute, avoidance of surgery as the third most important attribute, etc. A utility function may be generated for each patient type or for multiple patient types (e.g., to reduce the number of utility functions that need to be generated, although the generated utility functions may be less precise). Thus, the patient types may optionally be generated without making assumptions about the patient population, and instead patients are typed based on potential card choices a patient may make.

Optionally, in addition or instead, the CARDS database of possible rules can derive from simulated people generated from a population observation using a population algorithm which determines means, variances, and covariances with respect to their relative weightings on each of the treatment attributes. For example, the system may have prior data on real populations and may simulate a finite number of patients and cluster them into certain types of patients. In other words, if the distribution of population heterogeneity of preference may be measured in advance, simulated patients can be drawn from that distribution and allocated to rows of the CARDS database.

Optionally, an operator or other user can specify how many mistakes a patient is permitted to make in making card selections presented in choice questions. An example of a "mistake" would be where one set of the patient's selections indicate that attribute "A" is more important than attribute "B", and that another set of the patient's selections indicate that attribute "B" is more important than attribute "A". However, the more mistakes allowed, the more questions may need to be asked in certain situations in order to resolve such mistakes (e.g., determine which attribute is truly more important to the patient), and hence the longer the process may take. Optionally, the process can control the number of errors in violation of each possible scoring rule prior to eliminating that record (e.g., 0 errors, 1, error, 2 errors, etc.).

The following example illustration of an application of CARDS will refer back to the example above with respect to the application of ABC. Consider the same 16 cards as discussed above. If the "scoring rule" (utility function) for a patient is known, that scoring rule maps to a unique ordering of the cards. If there are 16 cards, there are 16! possible orderings, and 16! possible rows in the CARDS database. But more than 99% of the rows do not map perfectly or sufficiently to any reasonable scoring rule. That is, at least one pair of cards would be out of order, or "inconsistent," with any reasonable scoring rule. These types of errors have been an accepted part of conventional conjoint analysis, however certain embodiments of CARDS eliminates or significantly reduces these violated-pair errors and thereby both greatly speeds up the conjoint analysis process and significantly improves its quality. Thus, a given scoring rule implies a specific card order, and a specific card order that is perfectly consistent maps to a particular scoring rule among the records in the CARDS database. The scoring rule and the card order map to each other, and each such mapping is assigned a row in the CARDS database.

The CARDS application process will now be applied to an example set of 16 stimuli/cards. The combinations of CARDS and ABC may optionally enable a substantially accurate utility function to be generated for the 16 cards by presenting the user with only 10-12 sets of cards being presented to the patient (although greater or fewer sets may be presented, such as 6 sets, 8 sets, 14 sets or 16 sets).

State 1: Optionally all (or substantially all) orderings which do not perfectly map to a utility function are eliminated (excluded from consideration) from the CARDS database to ensure the orderings are consistent. For 16 cards, often less than 1% of the 16! possible orders are consistent, so the vast majority of possible card orderings are eliminated in advance because they include consistency errors. The CARDS algorithm starts with a listing, which may be in the form of database, including the consistent orderings. The list may be a vector of 16 card numbers in order from best to worst (or worst to best) according to a particular scoring rule, where each such vector answers all or substantially all $n(n-1)/2$ paired comparisons. The term "inconsistent," in this example refers to a particular pair of cards that are chosen by a patient in reverse order of preference, in contradiction to the best-fit scoring rule that explains the remainder of that patient's choices. Thus, there typically is not a mapping of a utility function to each possible card combinations. These types of inconsistency errors are very common in discrete choice experiments. By eliminating utility functions for which there are inconsistencies, the number of utility functions may be greatly reduced (e.g., by about 99% in some examples). As discussed elsewhere herein, in addition to using consistency to reduce the number of utility functions that need to be considered, the number of utility functions can optionally be further reduced by using a limited number of patient types to narrow the database (as similarly discussed elsewhere herein with respect to using a discretized version of the continuous multi-dimension space of possible utility functions) and/or clustering.

State 2: As similarly discussed above with respect to the example application of ABC, when a set of 4 cards are presented to a patient, and the patient indicates which is the best/most preferred card (set of treatment attributes) and which is the worst/least preferred card (set of treatment attributes), 5 of the 6 possible pairs in that question will have been directly answered/resolved. Those 5 paired answers can be compared against the CARDS database to identify which rows in the database have those 5 pairs in the same order. Other rows may be eliminated or marked as not relevant from the database. In this example, approximately $1/32=(1/2)^5$ rows of the database will remain at the end of each question. Optionally, historical responses to questions from other patients may be taken into account is selecting the 4 cards to present to the patient. For example, if a certain percentage of other patients (e.g., greater than 50%, greater than 75%, or other threshold) identify a first treatment option as a most preferred treatment option, and a certain percentage of other patients (e.g., greater than 50%, greater than 75%, or other threshold) identify a second treatment option as a least preferred treatment option, then the set of cards may include cards corresponding to the first treatment option and the second treatment option, and the other cards may optionally be chosen randomly. Optionally, as discussed elsewhere herein, the patient's selections may be entered into a table (see, e.g., FIG. 4), scores may be totaled, and the foregoing may be used to generate a utility function.

State 3: In addition, as similarly discussed above with respect to the application of the ABC technique, transitivity may be applied to identify extra paired comparison patient answers, which may be used to eliminate still additional rows in the database.

State 4: If the CARDS technique is combined with the ABC technique, then the ABC adaptive algorithm may be used determine the next 4 cards to show the patient, and more database rows will be eliminated, and so on, optionally until only one row is left. When the ABC technique is combined with the CARDS technique, unanswered pairs may be resolved on the basis that no rows remain in which Card 1>Card 2. Thus, in this example the database of all possible paired comparisons is scanned after the patient makes each choice, and records where those paired comparisons have been violated are eliminated. Thus, ABC and CARDS use a process of elimination to rapidly converge (e.g., optionally within substantially real time, such as within less than a second, or less than 10 seconds) to the scoring rule (e.g., a single scoring rule) that fits the observed choices of the patient.

State 5: If the CARDS technique is applied without utilizing the ABC technique, an adaptive algorithm may be used determine which 4 cards to show the patient next. For example, the adaptive algorithm may scan rows in the CARDS database which have not been eliminated from consideration to determine which 4 cards are expected to eliminate the greatest number of rows based on the individual's next choice. In an example embodiment, the adaptive algorithm identifies the greatest number of reversals of pairs in the rows. For example, if Card 4 and Card 7 appear 4-7 (4 preferred over 7) in half of the remaining rows (indicating that the item corresponding to Card 4 is preferred over the item corresponding to Card 7 based on that record's scoring rule), and 7-4 (7 before 4) in the other half of the remaining rows (indicating that the item corresponding to Card 7 is preferred over the item corresponding to Card 4), then Cards 4 and 7 are good candidates to be included in the next question as the patient's choice may eliminate half the rows. For example, if the cards presented to the patient include Card 4 (which may correspond to a first television set) and Card 7 (which may correspond to a second television set), and the patient selects Card 4 (the first television set) as the best/most preferred of the 4 cards and selects Card 7 (the second television set) as the worst/least preferred card, then the half of the rows/combinations where Card 7 is listed as more preferred than Card 4 can be eliminated as they do not match the patient's preferences.

To simplify programming, optionally, an array may be instantiated where the first column contains all of the pairings (120 pairs if there are 16 cards, as in state 1 of the ABC process described above), and the next two columns of the array are respectively left card-beats-right card and left beats right (although other arraignments are orderings of columns may be used). The values in this array may be counts from the database and a measure of how far apart they are in the rank orderings in the remaining records. Four cards are optionally selected which minimize a mathematical function of the absolute differences in the last two columns, so that the cards selected for presentation will, if selected by the patient as a best card or worst card, eliminate a large number of rows. Thus, in certain embodiments it may be advantageous to adaptively create the next choice set so as to resolve the greatest amount of uncertainty (or a relatively high amount of uncertainty), which is directly related to eliminating the greatest number of remaining records. If a particular card appears to dominate most other cards (more preferred as compared to most other cards), or to be dominated by most other cards (less preferred as compared to most other cards), it is less likely to appear in the next choice set. The CARDS process may continue selecting cards and posing questions to the patient until only one row remains. Even if the patient does not follow the process to its end, in which only one record remains, the subset of records remaining at any given point can be combined to estimate a scoring rule with some level of precision.

State 6: Even if approximately 99% of the rows are eliminated based on the consistency criteria, the remaining rows (1% of 16!) is on the order of ~200 billion, and so there is still a large number of rows to eliminate. Using conventional techniques to reduce the number of rows would require asking the patient to make such a large number of choices that the typical patient would be unable or would refuse to make such choices. Therefore, certain embodiments optionally utilize one or more techniques to significantly reduce the size of the database, and thereby reduce the number of questions that need be posed to the patient. For example, certain embodiments reduce the number of rows by reducing the resolution of patient types, by typing or clustering patients, where the number of patient types or clusters, and hence the number of utility functions, are reduced. The number of database rows may be referred to as the "resolution" of the database. Thus, there is a tradeoff between the questioning burden placed on patients and the level of resolution of the database. The fewer the number of patient types the fewer the number of questions. For example, a scoring rule may have seven coefficients based on patient priorities for attributes in that treatment category. Optionally, the resolution may be modified based at least in part on the patient's choices. Thus, reducing the number of attribute values greatly reduces the number of combinations, and therefore the number of database rows and size.

Referring now to the figures, FIG. 1 illustrates an example architecture. A patient preference evaluation system 100 includes a data store, which may be in the form of a database. The patient preference evaluation system 100 may be coupled over a network to one or more other external systems 102, 103 including respective data stores (e.g., databases). The external systems may store and provide data such as attribute data for various treatments for different medical conditions.

The patient preference evaluation system 100 may utilize the various data to generate rankings and/or scores for a patient for different treatments and/or treatment attributes for a given medical condition as described herein. The patient preference evaluation system 100 may be coupled to one or more user terminals 104, 106, 108 using a display interface. A given user terminal may be located in a medical establishment (e.g., a hospital or doctor's office), at a patient's home, or elsewhere. For example, the user terminal may be a wireless communication device of the patient or it may be a computer belonging to the medical establishment. The patient preference evaluation system 100 may transmit user interfaces for display to the user terminals 104, 106, 108 (e.g., cards and the reports) and receive patient input (e.g., patient indications via selection controls as to most and least preferred treatment options) via the user terminals 104, 106, 108, as discussed elsewhere herein. For example, the patient preference evaluation system 100 may provide user interfaces asking the patient to choose (indicate best and/or worst bundle of treatment attributes from a set of alternative treatment attributes) between various treatment options for a medical condition, and based at least in part on the patient's preference choices, generate and provide treatment attribute and/or treatment scores/rankings and/or reports. The foregoing systems and terminals may be connected via one or more networks 112 (e.g., the Internet, an intranet, etc.).

Figure 2:
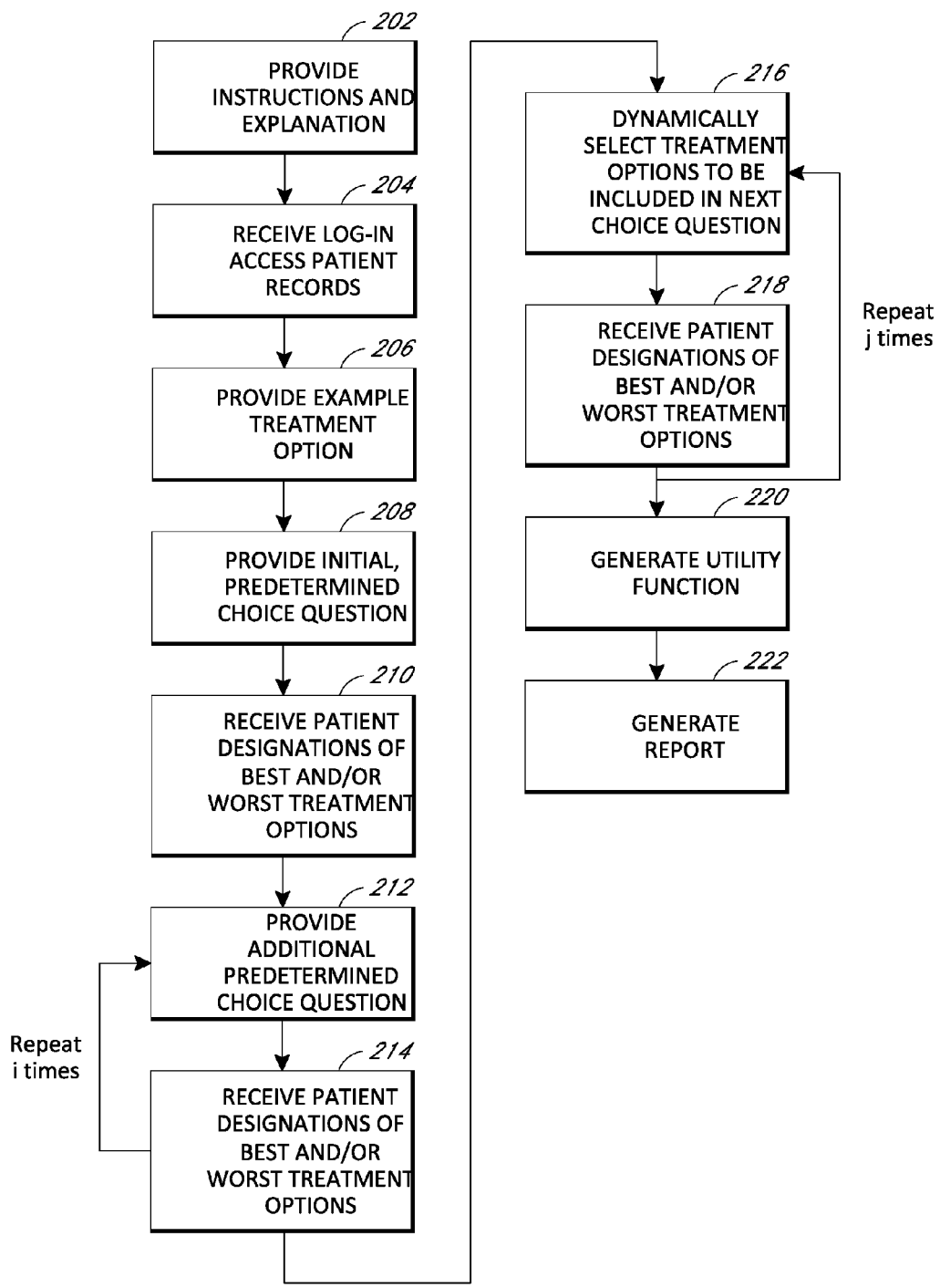
FIG. 2 illustrates an example process.

Referring now to FIG. 2, an example process for generating preference information for a given type of medical condition is illustrated. It is understand that while the following example may be refer to information and instructions being provided to a patient, such information and instructions may be instead or in addition provided to a doctor or other person. Further, the information provided by the patient may be entered into the system by another person. In addition, while the following example may be provided in the context of an example medical issue, the process may be similarly applied to other medical issues, using different interfaces. While certain example sets of medical treatment attributes may be discussed, other sets of attributes (with greater, fewer, or different attributes) may be used.

Figure 3A:
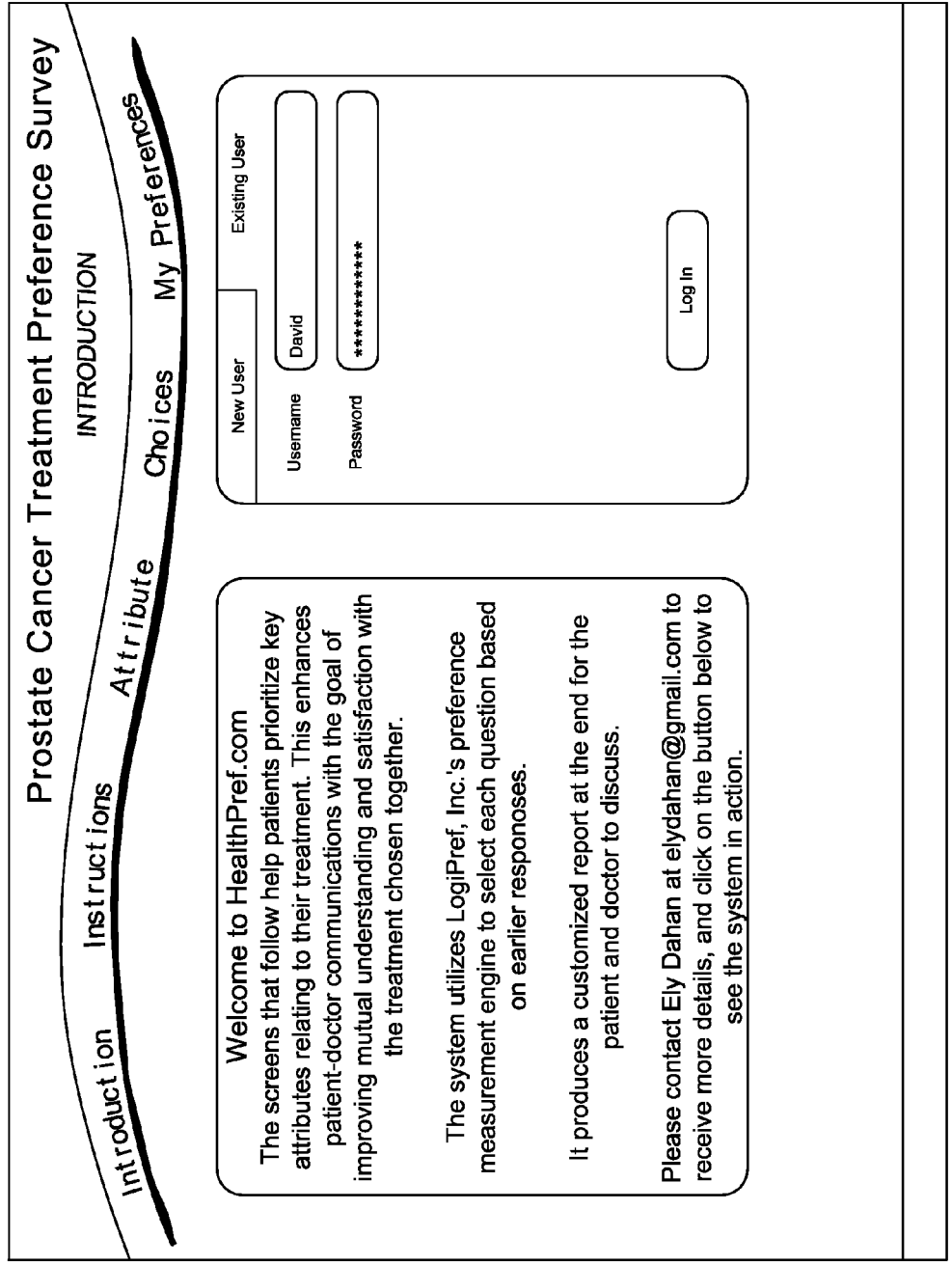
Figure 3D:
Figure 3E:
Figure 3F:
Figure 3H:
Figure 31:
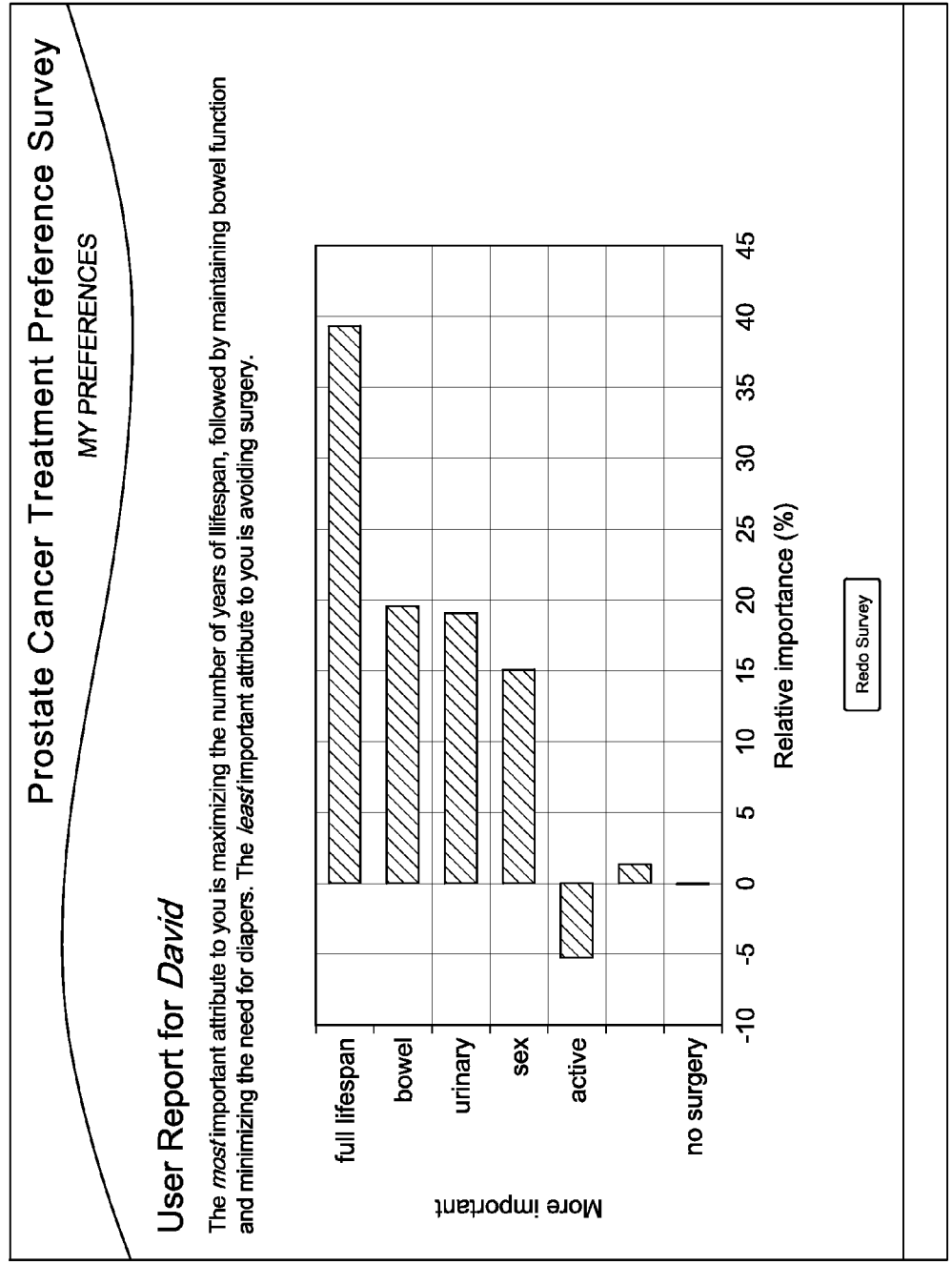

At state 202, a user interface is provided for display to a patient. Explanation and instructions are provided to the patient regarding the forthcoming preference process (sometimes referred to as a preference survey). For example, the patient may be informed that the patient will be asked to indicate preferences among different treatment options to help the patient prioritize attributes relating to their treatment. At state 204, a user interface may optionally be provided wherein the patient may be asked to enter a user identifier and/or a password, or may be asked to confirm identification presented to the patient. The system may then use such login information received via the user interface to locate the patient's record(s). Logging in by the patient may enable the patient's choices to be recorded in association with the patient's medical records and may be used to select the appropriate pool of medical treatment options that corresponds to the patient's condition (as indicated by the patient's medical records identified via the log in information). An example of such an interface is illustrated in FIG. 3A.

More detailed instructions may be further provided to the patient. In this example, the patient may be informed that the patient will be presented with a series of treatment option sets from which the patient will be asked to identify the best option (from the patient's perspective) and the worst option (from the patient's perspective). In this example, with 16 treatment options, the user is informed that the user will be asked to provide best/worst feedback for 10-12 sets of treatment options based on the associated treatment attributes.

At state 206, a user interface may be provided for display to the patient, providing an example of a treatment option and associated attributes. In this example, the medical issue being treated is prostate cancer, and the example attributes may include treatment issues ("doctor and family support this treatment," "treatment requires action within weeks," "treatment does not require surgery"), and side effects ("sex: same as before treatment," "urinary: short term problems," "bowel: long term problems," "Lifespan: Live my expected lifespan"). If the user selects a given attribute, more information or comments may be provided for display to the user (e.g., if the user selects "Sex", the comment may be "Sex: 'If you have an understanding partner, the ED (erectile dysfunction) thing can be OK.'"). The user interface may further explain that each treatment option will be presented as a "bundle of attributes," (7 attributes in this example). A control is provided which the patient can activate to begin the survey process.

At state 208, a determination is made that the patient activated the control to begin the survey process, and several treatment options (comprising bundles of attributes) are displayed from which the patient is to indicate a most preferred option and a least preferred option. An example of such an interface is illustrated in FIG. 3B. In this example, the patient is presented with four treatment options, each with seven attributes, where each treatment option has a unique combination of attributes relative to the other presented treatment options (although there may be overlap). For example, if the patient selects the third option as the most preferred option ("doctor and family do not favor this treatment," "treatment allows months or longer for decision," "treatment does not require surgery" "sex: same as before treatment," "urinary: Longer-term issues," "bowel: No problems," "Lifespan: Live 5 years fewer than expected"), the system will receive and store the selection and may determine that the patient is willing to override the advice of the patient's family and doctor (and so the attribute of doctor and family support may be assigned a low weighting), and that the patient is very adverse to surgery. This determination may optionally be further refined as the patient continues to provide feedback on the subsets of treatment options in the choice questions. At state 210, the system receives and stores the patient's "best" and "worst" selection.

For example, at state 212, another subset of treatment options may be presented to the patient in the form of a choice question, and the patient is again asked to indicate a most preferred option and a least preferred option. An example of such an interface is illustrated in FIG. 3C. At state 214, the system will receive and store the selection. The selection process may be repeated with still more choice questions, including subsets of treatment options (e.g., i number of subsets/choice questions), as illustrated in FIGS. 3D-3H. As similarly discussed above, a first number of subsets may be selected for inclusion in respective choice questions without reference to previous selections made by the patient with respect earlier choice questions (e.g., the grouping of the subset of treatment options presented in choice questions illustrated FIGS. 3B-3E may optionally be made independent of the selections made by the patient with respect to the subsets of treatment options presented in FIGS. 3B-3E).

At state 216, one or more subsets of treatment options (e.g., a variable j number of subsets) may be dynamically selected for inclusion in respective choice questions based at least in part on one or more previous most preferred/least preferred selections may by the patient with respect to the pool of treatment options. For example, the subset of treatment options presented in FIG. 3F may be made by the system based on the most preferred/least preferred selections made by the patient with respect to the subsets of options presented in FIGS. 3B-3E; and the subset of options presented in FIG. 3G may be made by the system based on the most preferred/least preferred selections made by the patient with respect to the subsets of options presented in FIGS. 3B-3F, and so on. The number of dynamically generated choice questions may also be dynamically determined, where the number of choice questions needed to come to an adequate determination as to the patient's preferences may depend on selections made by the patient with respect to previous choice questions. At state 218, the system will receive and store the patient's selections with respect to the dynamically generated choice question. This process may be repeated (e.g., a j number of times). In this example, 11 choice questions are dynamically generated, while 4 choice questions are predetermined/fixed.

At state 220, the system may optionally generate, optionally in substantially real-time, one or more utility functions based at least in part on the patient selections discussed above, and may use the utility function to rank and/or score the various treatment actions.

At state 222, the system may generate a report patient based on the patient's selections (optionally using the utility function), that summarizes the patient's treatment preferences with respect to various treatment attributes. The report may include graphs, text, and images.

FIG. 3I illustrates an example user report generated for a patient based on the patient's most preferred/least preferred selections. This report summarizes the patient's treatment preferences and priorities, and serves to enhance the doctor-patient discussion of possible treatments. In this example, the patient was presented with 15 choice questions (4 static choice questions, and 11 dynamically generated choice questions), each with 4 alternative treatment options, and each treatment option comprising 7 attributes. In this example, the report includes both a textual summary and a graph. The text summary lists which attribute is most important to the patient (e.g., based on the patient tending to select treatment options that have that attribute), which attribute is the second most important attribute, which attribute is the least import attribute, and so on. Optionally, the text does not provide the attribute ranking for all of the attributes, although optionally the text does provide the attribute ranking for all of the attributes. In this example, a bar graph is generated, with a bar for each of the attributes (although optionally only a subset of attributes may instead be presented). In this example, the Y-axis corresponds to the importance ranking of the attributes, and the X-axis corresponds to the relative importance of each attribute. The relative importance may optionally be determined by taking the range of each attribute's utility score divided by the sum of the range of scores for all the attributes. For example, if there are 7 attributes, if a given attribute has a range of scores of "0", then that attribute may have a relative importance of 0/100 (assuming 100 is the sum of the range of scores for all the attributes). If a given attribute has a range of scores of "50," then that attribute may have a relative importance of 50/100, and so on.

Thus, a doctor may use such reported preference information to identify suitable medical treatments that have attributes that match, or that reasonably match the patient's preferences. For example, if the lifespan preference is the most highly ranked, that doctor will understand that the patient may be most desirous of a treatment that enhances the patient's lifespan, even if it results in side effects such as decreased sexual activity or incontinence, and even if the patient's family does not approve of such a treatment. Of course, the doctor can recommend a treatment that does not match the patient's preferences or that only matches the patient's preferences partially, if the doctor feels that such treatment is in the best interests of the patient.

Figure 4:
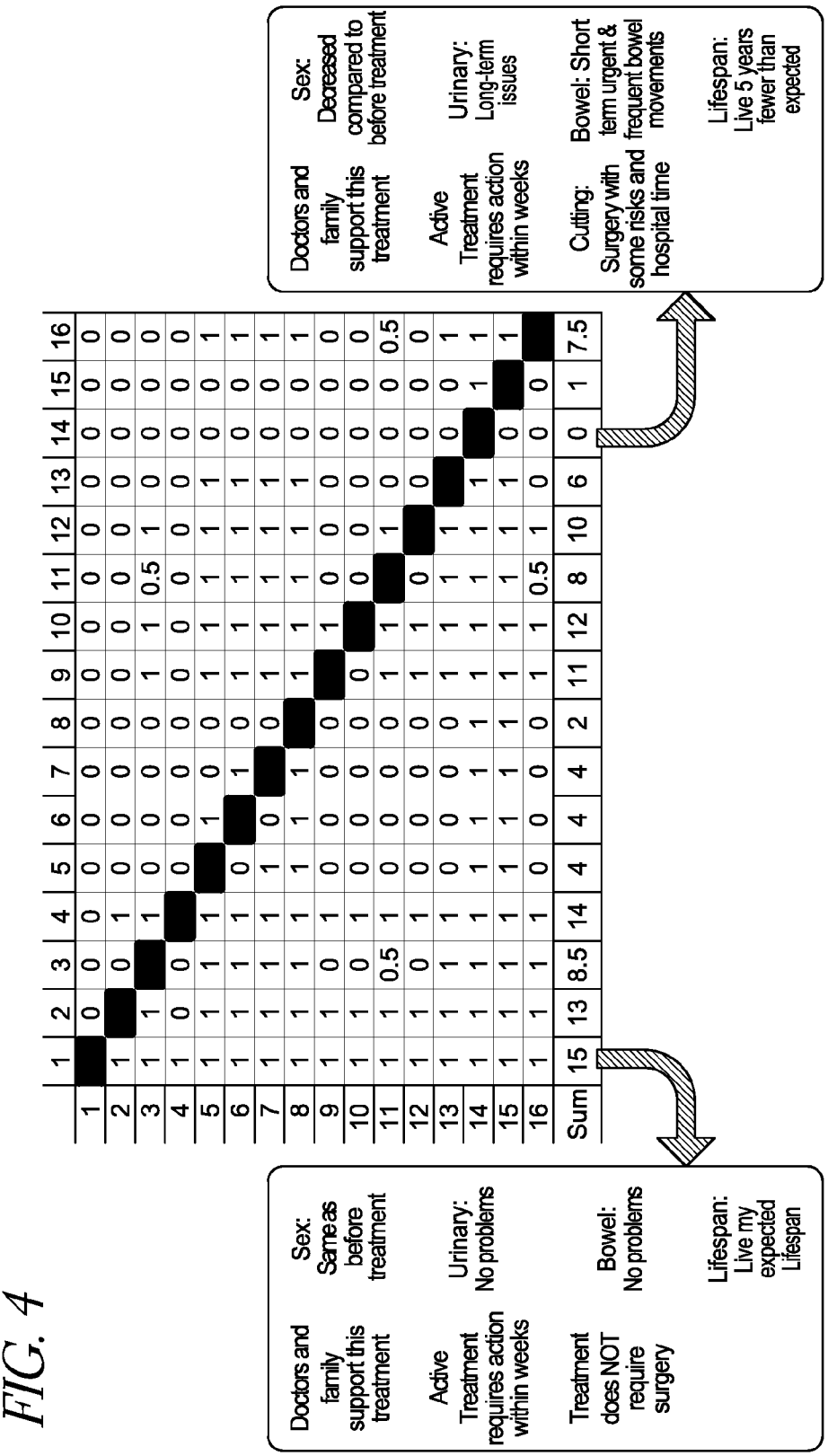
FIG. 4 illustrates an example bundle of attributes scoring table.

FIG. 4 illustrates an example table generated by the system based on the patient selections, to determine using paired comparisons which attributes were preferred by the patient relative to other attributes. Each number in the row and column headings corresponds to a card (a treatment option). In this example, there are 16 cards, and card 1 was preferred over all other 15 cards, and so receives a score of 15. Card 2 was preferred over all other cards, except cards 1 and 4 (which were preferred over card 2), and so receives a score of 13 (15-2). Card 3 was preferred over all other cards, except cards 1, 2, 4, 9, 10, and 12, and was tied with card 11 (which is scored as 0.5), and so receives a score of 8.5 (15-6.5). The other cards are similarly scored. The scoring table may be used to generate the attribute rankings and the relative importance of a given attribute using multiple linear regression or other analysis. Thus, the table may optionally be examined statistically to generate a utility function. Optionally, the table may be initialized to all zeros (so that all attributes are tied, each with a score of 0). The table may then be filled in based on the patient's selections, as noted above. Optionally, even if the patient does not complete all the selections, and the table is not completely filled in, the system may still generate estimates with respect to the attribute rankings and scores, although the estimates may be less accurate in some cases.

Thus, as described above, certain embodiment facilitate the quick, efficient, and accurate determination of a patient's preferences with respect to various medical treatment attributes, without overwhelming the patient with complex demands for information.

Unless otherwise indicated, the functions described herein may be performed by software (e.g., including modules) including executable code and instructions running on one or more systems including one or more computers. The software may be stored in computer readable media (e.g., some or all of the following: optical media (e.g., CD-ROM, DVD, Blu-ray, etc.), magnetic media (e.g., fixed or removable magnetic media), semiconductor memory (e.g., RAM, ROM, Flash memory, EPROM, etc.), and/or other types of computer readable media.

The one or more computers can include one or more central processing units (CPUs) that execute program code and process data, non-transitory, tangible memory, including. for example, one or more of volatile memory, such as random access memory (RAM) for temporarily storing data and data structures during program execution, non-volatile memory, such as a hard disc drive, optical drive, or FLASH drive, for storing programs and data, including databases," a wired and/or wireless network interface for accessing an intranet and/or Internet, and/or other interfaces.

In addition, the computers can include a display for displaying user interfaces, data, and the like, and one or more user input devices, such as a keyboard, mouse, pointing device, touch screen, microphone and/or the like, used to navigate, provide commands, enter information, provide search queries, and/or the like. The systems described herein can also be implemented using general-purpose computers, special purpose computers, terminals, state machines, and/or hardwired electronic circuits.

While various systems are described herein optionally some are or all of the various systems can be included a single system operated by a single operator.

The example processes described herein do not necessarily have to be performed in the described sequence, and not all states have to be reached or performed.

Unless the context otherwise indicates, the term "field" with respect to a user interface or form is intended to refer to a user entry mechanism via which the user can input data or commands, such as a text field, a menu via which the user can make a selection, etc. While reference may be made to applying certain embodiments with respect determining a patient's preferences with respect to medical treatments and medical treatment attributes, it is understood that such embodiments may be utilized to determining a person's preferences with respect to other services and products.

Various embodiments provide for communications between one or more systems and one or more users. These user communications may be provided to a terminal (e.g., an Interactive television, a phone, a video game system, a laptop/desktop computer, a device providing Internet access, or other networked device). For example, communications may be provided via Webpages, downloaded documents, email, SMS (short messaging service) message, MMS (multimedia messaging service) message, terminal vibrations, other forms of electronic communication text-to-speech message, otherwise.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

What is claimed is:

1. A method of evaluating patient preferences, the method comprising:
    identifying a set of treatment options for a first medical condition, wherein a given treatment option comprises a plurality of attributes including side effects and attributes other than side effects;
    identifying a first subset of treatment options from the set of treatment options for the first medical condition;
    providing for display to a first patient the first subset of treatment options;
    receiving at a computer system an indication from the first patient of a most preferred treatment option and a least preferred treatment option of the first subset of treatment options, wherein the first patient does not provide additional feedback regarding other treatment options in the first subset of treatment options;
    identifying a second subset of treatment options from the set of treatment options for the first medical condition, the first subset different than the second subset;
    providing for display to the first patient the second subset of treatment options;
    receiving an indication from the first patient of a most preferred treatment option and a least preferred treatment option of the second subset of treatment options, wherein the first patient does not provide additional feedback regarding other treatment options in the second subset of treatment options;
    based at least in part on the indications received from the first patient regarding the first subset of treatment options and the second subset of treatment options, dynamically and adaptively generating by the computer system, in substantially real time, a third subset of treatment options from the set of treatment options for the first medical condition, the third subset different than the first and second subsets;
    receiving an indication from the first patient of a most preferred treatment option and a least preferred treatment option of the third subset of treatment options;
    based at least in part on the indications received from the first patient regarding the first subset of treatment options, the second subset of treatment options, and the third subset of treatment options, determining, by the computer system, weightings for attributes associated with the set of treatment options;
    generating in substantially real-time, by the computer system, a utility function based at least in part on the weightings;
    using, by the computer system, the utility function to generate, in substantially real-time, scoring information, ranking information, or both scoring information and ranking information with respect to the plurality of attributes of the set of treatment options;
    reporting, in substantially real-time, by the computer system, at least a portion of the scoring information, at least a portion of the ranking information, or at least a portion of both the scoring information and the ranking information.

2. The method as defined in claim 1, wherein the ranking information comprises scoring information.

3. The method as defined in claim 1, wherein the first subset of treatment options comprises at least four treatment options.

4. The method as defined in claim 1, wherein the first subset of treatment options consists of four treatment options.

5. The method as defined in claim 1, the method further comprising using transitivity to dynamically generate by the computer system, in substantially real time, the third subset of treatment options based at least in part on the indications received from the first patient regarding the first subset of treatment options and the second subset of treatment options.

6. The method as defined in claim 1, wherein the plurality of attributes comprise family support and surgery.

7. The method as defined in claim 1, wherein the side effects comprise effect on patient life span.

8. The method as defined in claim 1, wherein the first subset of treatment options are grouped together based at least in part on their respective attribute values.

9. The method as defined in claim 1, wherein the third subset of treatment options includes at least one treatment option from the first set subset of treatment options and at least one treatment option from the first second subset of treatment options.

10. The method as defined in claim 1, wherein adaptively selecting the third subset of treatment options comprises selecting treatment options that resolve a greatest number of unresolved pairs, among possible pairs, of treatment options.

11. The method as defined in claim 1, the method further comprising determining, utilizing transitivity, whether the first patient prefers a first treatment option over a second treatment option, without presenting first and second treatment options together to the patient, based at least on a previous preference indication from the user with respect to the first treatment option when presented with a treatment option different than the second treatment option.

12. A system, comprising:
    a computing device comprising one or more processors;
    a non-transitory data store coupled to the processing device, the data store storing a set of treatment options for a first medical condition, wherein a given treatment option comprises a plurality of attributes including side effects and attributes other than side effects;
    a display interface coupled to the computing device; and
    non-transitory media that stores program code that when executed by the computing device causes the system to perform operations comprising:
        accessing, from the non-transitory data store, a first subset of treatment options from the set of treatment options for the first medical condition;
        causing, using the display interface, the first subset of treatment options to be displayed to a first patient;
        instructing the first patient to select a most preferred treatment option, a least preferred treatment option, or a most preferred treatment option and a least preferred treatment option of the first subset of treatment options;

receiving an indication from the first patient of a most preferred treatment option, or a least preferred treatment option, or a most preferred treatment option and a least preferred treatment option of the first subset of treatment options, wherein the first patient does not provide additional feedback regarding other treatment options in the first subset of treatment options;

identifying a second subset of treatment options from the set of treatment options for the first medical condition, the first subset different than the second subset;

causing, using the display interface, the second subset of treatment options to be displayed to the first patient;

receiving an indication from the first patient of a most preferred treatment option, or a least preferred treatment option, or a most preferred treatment option and a least preferred treatment option of the second subset of treatment options;

based at least in part on the indications received from the first patient regarding the first subset of treatment options and the second subset of treatment options, dynamically and adaptively generating, in substantially real time, a third subset of treatment options from the set of treatment options for the first medical condition, the third subset different than the first and second subsets;

receiving an indication from the first patient of a most preferred treatment option, or a least preferred treatment option, or a most preferred treatment option and a least preferred treatment option of the third subset of treatment options;

based at least in part on the indications received from the first patient regarding the first subset of treatment options, the second subset of treatment options, and the third subset of treatment options, generating in substantially real-time a utility function;

using the utility function to generate, in substantially real-time, scoring information, ranking information, or both scoring information and ranking information with respect to the plurality of attributes of the set of treatment options;

reporting, by the computer system, at least a portion of the scoring information, at least a portion of the ranking information, or at least a portion of both the scoring information and the ranking information.

13. The system as defined in claim 12, wherein the first subset of treatment options comprises at least four treatment options.

14. The system as defined in claim 12, the operations further comprising using transitivity to dynamically generate, in substantially real time, the third subset of treatment options based at least in part on the indications received from the first patient regarding the first subset of treatment options and the second subset of treatment options.

15. The system as defined in claim 12, wherein the plurality of attributes comprise family support and surgery.

16. The system as defined in claim 12, wherein the side effects comprise effect on patient life span.

17. The system as defined in claim 12, wherein the first subset of treatment options are grouped together based at least in part on their respective attribute values.

18. The system as defined in claim 12, wherein the third subset of treatment options includes at least one treatment option from the first set subset of treatment options and at least one treatment option from the first second subset of treatment options.

19. The system as defined in claim 12, wherein adaptively selecting the third subset of treatment options comprises selecting treatment options that resolve a greatest number of unresolved pairs, among possible pairs, of treatment options.

20. The system as defined in claim 12, the operations further comprising determining, utilizing transitivity, whether the first patient prefers a first treatment option over a second treatment option, without presenting first and second treatment options together to the patient, based at least on a previous preference indication from the user with respect to the first treatment option when presented with a treatment option different than the second treatment option.

21. Non-transitory media that stores program code that when executed by a computing system causes the system to perform operations comprising:

accessing, from a non-transitory data store storing a set of treatment options for a first medical condition, wherein a given treatment option comprises a plurality of attributes including side effects and attributes other than side effects, a first subset of treatment options from the set of treatment options for the first medical condition;

enabling the first subset of treatment options to be displayed to a first patient;

instructing the first patient to select a most preferred treatment option, a least preferred treatment option, or a most preferred treatment option and a least preferred treatment option of the first subset of treatment options;

receiving an indication from the first patient of a most preferred treatment option, a least preferred treatment option, or a most preferred treatment option and a least preferred treatment option of the first subset of treatment options;

identifying a second subset of treatment options from the set of treatment options for the first medical condition, the first subset different than the second subset;

enabling the second subset of treatment options to be displayed to the first patient;

receiving an indication from the first patient of a most preferred treatment option, a least preferred treatment option, or a most preferred treatment option and a least preferred treatment option of the second subset of treatment options;

based at least in part on the indications received from the first patient regarding the first subset of treatment options and the second subset of treatment options, dynamically and adaptively generating, in substantially real time, a third subset of treatment options from the set of treatment options for the first medical condition, the third subset different than the first and second subsets;

receiving an indication from the first patient of a most preferred treatment option, a least preferred treatment option, or a most preferred treatment option and a least preferred treatment option of the third subset of treatment options;

based at least in part on the indications received from the first patient regarding the first subset of treatment options, the second subset of treatment options, and the third subset of treatment options, generating in substantially real-time a utility function;

using the utility function to generate, in substantially real-time, scoring information, ranking information, or both scoring information and ranking information with respect to the plurality of attributes of the set of treatment options;

reporting at least a portion of the scoring information, at least a portion of the ranking information, or at least a portion of both the scoring information and the ranking information.

22. The non-transitory media as defined in claim 21, wherein the first subset of treatment options comprises at least four treatment options.

23. The non-transitory media as defined in claim 21, the operations further comprising using transitivity to dynamically generate, in substantially real time, the third subset of treatment options based at least in part on the indications received from the first patient regarding the first subset of treatment options and the second subset of treatment options.

24. The non-transitory media as defined in claim 21, wherein the plurality of attributes comprise family support and surgery.

25. The non-transitory media as defined in claim 21, wherein the side effects comprise effect on patient life span.

26. The non-transitory media as defined in claim 21, wherein the first subset of treatment options are grouped together based at least in part on their respective attribute values.

27. The non-transitory media as defined in claim 21, wherein the third subset of treatment options includes at least one treatment option from the first set subset of treatment options and at least one treatment option from the first second subset of treatment options.

28. The non-transitory media as defined in claim 21, wherein adaptively selecting the third subset of treatment options comprises selecting treatment options that resolve a greatest number of unresolved pairs, among possible pairs, of treatment options.

29. The non-transitory media as defined in claim 21, the operations further comprising determining, utilizing transitivity, whether the first patient prefers a first treatment option over a second treatment option, without presenting first and second treatment options together to the patient, based at least on a previous preference indication from the user with respect to the first treatment option when presented with a treatment option different than the second treatment option.

* * * * *

UNITED STATES PATENT AND TRADEMARK OFFICE
CERTIFICATE OF CORRECTION

PATENT NO. : 8,762,177 B2
APPLICATION NO. : 14/025209
DATED : June 24, 2014
INVENTOR(S) : Eliav Dahan It is certified that error appears in the above-identified patent and that said Letters Patent is hereby corrected as shown below:

On The Title Page

Page 1 (item 73, Assignee) at line 1, Change "Logipref," to --LogiPref,--.

Page 1 (item 74, Attorney) at line 19, Change "Knobbem" to --Knobbe,--.

In The Drawings

Sheet 3 of 12 (FIG. 3A) at line 12 (approx.), Change "responoses." to --responses.--.

Sheet 11 of 12 (FIG. 3I) at line 4 (approx.), Change "llifespan," to --lifespan,--.

In The Specification

In column 11 at line 8, Change "patients" to --patients.--.

In column 16 at line 47, Change "may by" to --may be--.

Signed and Sealed this
Thirteenth Day of January, 2015

Michelle K. Lee
*Deputy Director of the United States Patent and Trademark Office*